United States Patent [19]

Wright

[11] Patent Number: 5,618,840
[45] Date of Patent: Apr. 8, 1997

[54] ANTIBACTERIAL OIL-IN-WATER EMULSIONS

[75] Inventor: D. Craig Wright, Gaithersburg, Md.

[73] Assignee: Novavax, Inc., Columbia, Md.

[21] Appl. No.: 443,937

[22] Filed: May 18, 1995

Related U.S. Application Data

[63] Continuation-in-part of Ser. No. 329,730, Oct. 26, 1994, abandoned, which is a continuation-in-part of Ser. No. 322,827, Oct. 13, 1994, Pat. No. 5,549,901, which is a continuation-in-part of Ser. No. 246,868, May 20, 1994, Pat. No. 5,547,677.

[51] Int. Cl.$^6$ ..................................................... A61K 7/40
[52] U.S. Cl. ......................... 514/549; 514/552; 514/943
[58] Field of Search ................................... 514/943, 549, 514/552

[56] References Cited

U.S. PATENT DOCUMENTS

| | | | |
|---|---|---|---|
| 4,006,218 | 2/1977 | Sipos | 424/54 |
| 4,091,090 | 5/1978 | Sipos | 424/45 |
| 4,197,318 | 4/1980 | Sipos | 424/326 |
| 4,230,702 | 10/1980 | Eckert et al. | 514/943 |
| 4,321,257 | 3/1982 | Sipos | 424/54 |
| 4,323,551 | 4/1982 | Parran, Jr. | 424/54 |
| 4,348,415 | 9/1982 | Tsutsumi et al. | 514/943 |
| 4,474,748 | 10/1984 | Sipos | 424/40 |
| 4,902,720 | 2/1990 | Baldone et al. | 424/54 |
| 4,997,851 | 3/1991 | Isaacs et al. | 514/552 |
| 5,039,688 | 8/1991 | Lewis et al. | 424/54 |
| 5,143,934 | 9/1992 | Lading et al. | 514/943 |
| 5,176,901 | 1/1993 | Gallopo et al. | 424/54 |
| 5,300,305 | 4/1994 | Stapler et al. | 424/490 |
| 5,362,494 | 11/1994 | Zysman et al. | 424/54 |
| 5,403,587 | 4/1995 | McCue et al. | 514/943 |
| 5,534,544 | 7/1996 | Plaut et al. | 514/552 |
| 5,550,145 | 8/1996 | Olund et al. | 514/552 |

OTHER PUBLICATIONS

Isaacson, P.G., "Gastric Lymphoma and *Helicobacter Pylori*" *New England Journal of Medicine*, vol. 330, No. 18, pp. 1310–1311, 5 May 1994;.

Parsonnet, J. et al., "*Helicobacter Pylori* Infection and Gastric Lymphoma" *New England Journal of Medicine*, vol. 330, No. 18, pp. 1267–1271, 5 May 1994.

Pinnaduwage, P. et al., "Use Of A Quaternary Ammonium Detergent In Liposome Mediated DNA Transfection Of Mouse L–Cells", *Biochimica et Biophysica Acta*, vol. 985, pp. 33–37, 1989.

*McCutcheon's Detergents & Emulsifers 1971 Annual*, (New Jersey: Allured Publishing Company 1971), pp. 49,86.

*Remington's Pharmaceutical Sciences* (1985), 17th Edition: pp. 317–318, 328.

Merck Index, (I), 10th Ed., pp. 281–282, 979–8° (1985).

Merck Index (II), 10th Ed, p. 312 (1985).

*Primary Examiner*—James H. Reamer

[57] ABSTRACT

An antibacterial oil-in-water emulsion for inhibiting the growth of *Helicobacter pylori* is disclosed. The oil-in-water emulsion of the invention comprises droplets of an oily discontinuous phase dispersed in a continuous phase. The oily discontinuous phase contains an oil carrier and a glycerol ester selected from the group consisting of glycerol monooleate and glycerol monostearate. The emulsion can be positively charged, negatively charged or chargeless. In one embodiment, the emulsion is positively charged and further comprises a cationic halogen-containing compound having a $C_{12}$–$C_{16}$ chain as a positive charge producing agent. In another embodiment, the emulsion is negatively charged and further comprises an negative charge producing agent having a $C_{12}$–$C_{22}$ chain. The disclosed emulsions can be administered to individuals, for example, orally, to treat or prevent *Helicobacter pylori* infections.

9 Claims, No Drawings

ANTIBACTERIAL OIL-IN-WATER EMULSIONS

RELATED APPLICATIONS

This application is a continuation-in-part of U.S. Ser. No. 08/329,730, entitled "Virus Inactivating Oil-In-Water Emulsions", filed Oct. 26, 1994, now abandoned which is a continuation-in-part of U.S. Ser. No. 08/322,827, entitled "Antimicrobial Oil-In-Water Emulsions", filed Oct. 13, 1994, Pat. No. 5,549,901, which is a continuation-in-part of U.S. Ser. No. 08/246,868, entitled "Antimicrobial Oil-in-Water Emulsions", filed May 20, 1994, Pat. No. 5,547,677 the contents of which are incorporated herein by reference.

BACKGROUND OF THE INVENTION

The present invention relates to a lipid-containing oil-in-water emulsion which inactivates bacteria, particularly *Helicobacter pylori*, upon contact.

It is known that if a water-immiscible liquid phase is mixed into an aqueous phase by mechanical agitation, for example, by means of an ultra-disperser, the stability of the resulting oil-in-water dispersion most frequently requires the addition of an emulsifying agent, the molecules of which are adsorbed onto the surface of the oil droplets to form a kind of continuous membrane which prevents direct contact between two adjacent droplets. The drops of oil can further contain substances soluble in an organic medium, such as a sterol.

In addition to discrete oil droplets dispersed in an aqueous phase, oil-in-water emulsions can also contain other lipid structures, such as small lipid vesicles (i.e., lipid spheres which often consist of several substantially concentric lipid bilayers separated from each other by layers of aqueous phase), micelles (i.e., amphiphile molecules in small clusters of 50–200 molecules arranged so that the polar head groups face outward toward the aqueous phase and the apolar tails are sequestered inward away from the aqueous phase), or lamellar phases (lipid dispersions in which each particle consists of parallel amphiphile bilayers separated by thin films of water). These lipid structures are formed as a result of hydrophobic forces which drive apolar residues (i.e., long hydrocarbon chains) away from water.

*Helicobacter pylori* is a spiral shaped, urease producing bacterium that lives at the gastric epithelium-mucus junction and causes antral gastritis, peptic ulcer disease, gastric non-Hodgkin's lymphoma and gastric carcinoma. The bacterium is believed to be transmitted directly from person to person since no non-human reservoir has been identified (Berkowicz et al. (1987) *Lancet* 680–81). The portals of entry of pathogenic bacteria such as *Helicobacter pylori* are predominantly the skin and mucus membranes, including the upper and lower respiratory tracts. The first step in any infection is attachment or colonization on skin or mucus membranes with subsequent invasion and dissemination of the bacterium.

Thus far, therapy with bismuth and antibiotics has generally not been successful in irradicating the bacterium and preventing colonization (Rauws et al. (1988) *Gastroenterology* 94:33–40). It is therefore one object of the present invention to provide an alternative approach to inactivating bacteria such as *Helicobacter pylori* upon contact.

SUMMARY OF THE INVENTION

The present invention provides a stable antibacterial oil-in-water emulsion for inactivating bacteria, particularly gram negative bacteria such as *Helicobacter pylori*, upon contact. The emulsion comprises droplets of an oily "discontinuous phase" dispersed in an aqueous "continuous phase". The discontinuous phase of the emulsion can be positively charged, negatively charged, or chargeless, and contains at least one emulsifier and an oil carrier. The primary emulsifier comprises a glycerol ester including, but not limited to, glycerol monooleate (GMO), glycerol trioleate (GTO), glycerol monolaurate (GML), glycerol dilaurate (GDL), and glycerol monostearate (GMS). Preferred glycerol esters for use in forming the oily discontinuous phase are GMO and GMS. In one embodiment of the invention, at least a portion of the emulsion may be in the form of lipid structures including, but not limited to, unilamellar, multilamellar, and paucilamellar lipid vesicles, micelles, and lamellar or hexagonal phases.

Oils useful in forming the oily discontinuous phase include a broad spectrum of water-immiscible materials, such as soybean oil, avocado oil, squalene oil, sesame oil, olive oil, canola oil, corn oil, rapeseed oil, safflower oil, sunflower oil, fish oils, flavored oils, water insoluble vitamins, and mixtures thereof.

The oily discontinuous phase of the emulsion can further include a positive or negative charge producing agent. Positive charge producing agents for use in the invention are preferably cationic halogen-containing compounds having a $C_{12}$–$C_{16}$ chain. In a preferred embodiment, the cationic halogen-containing compound having a $C_{12}$–$C_{16}$ chain is selected from the group consisting of cetylpyridinium chloride (CPC), cetypyridinium bromide (CPB), and cetyltrimethylammonium bromide (CTAB). Negative charge producing agents which can be used are preferably anionic compounds having a $C_{12}$–$C_{22}$ chain, most preferably organic acids. In a preferred embodiment of the invention, the negative charge producing agent is oleic acid.

The oily discontinuous phase can further contain at least one sterol selected from the group consisting of cholesterol, cholesterol derivatives, hydrocortisone, phytosterol, and mixtures thereof. The term "cholesterol derivatives," as used herein, includes but is not limited to sulfate and phosphate derivatives of cholesterol. Preferred sterols include phytosterols such as soya sterol.

Antibacterial emulsions of the present invention are non-toxic and safe, for example, when swallowed, inhaled, or applied to the skin. This result is unexpected, particularly for the positively charged emulsions of the invention, since many cationic halogen-containing compounds having a $C_{12}$–$C_{16}$ chain are extremely toxic if administered alone. For example, cetylpyridinium chloride (CPC), a preferred cationic halogen-containing compound of the invention, causes severe irritation and damage to tissues of the upper respiratory tract, mucous membranes and skin if administered alone. However, when administered in the form of an emulsion of the invention, no such adverse effects occur. Furthermore, the emulsions of the invention are stable when heated or exposed to significant levels of acid and base.

The antibacterial emulsions of the present invention can be used, for example, in pharmaceutical preparations (e.g., creams, solutions and suspensions) to inhibit the growth of bacteria, particularly encapsulated bacteria such as *Helicobacter pylori*, which have relatively rough LPS types compared to the other gram negative bacteria. Accordingly, the present invention also provides an antibacterial preparation suitable for pharmaceutical administration made up of an antibacterial emulsion of the invention and a pharmaceutically acceptable carrier.

The preparation can be applied topically to skin surface areas, mucus membranes, or oral surfaces, for example, as a cream, gel, spray, or mouthwash to treat or prevent bacterial infections. Alternatively, the preparation can be administered enterally to inactivate pathogenic bacteria such as *Helicobacter pylori*. Accordingly, the present invention further provides a method for inhibiting the growth of a bacterium in an individual, particularly *Helicobacter pylori*, by oral or systemic administration of the antibacterial emulsion of the invention to the individual.

DETAILED DESCRIPTION OF THE INVENTION

The present invention relates to a stable antibacterial oil-in-water emulsion made of droplets of an oily discontinuous phase containing at least one emulsifier dispersed in an aqueous continuous phase.

The term "antibacterial," as used herein, means having the ability to inactivate a bacterium, particularly a gram negative bacteria such as Helicobacter .priori. The term "inactivate", as used herein, includes but is not limited to, killing or inhibiting growth of the bacterium. It appears that such inactivation occurs by disruption of the bacterial membrane. Accordingly, one aspect of the present invention provides an antibacterial oil-in-water emulsion which disrupts the membrane structure of a bacterium, such as *Helicobacter pylori*, so that the bacterium is inactivated.

The term "emulsion," as used herein, includes both classic oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar and hexagonal phases.

The oily discontinuous phase of the emulsions of the present invention comprises, at least in part, a primary emulsifier and an oil carrier. The term "primary emulsifier" refers to the emulsifier which constitutes the greatest proportion by weight of any single emulsifier contained in the oily discontinuous phase, and which is preferably a glycerol ester. The oily discontinuous phase can further contain at least one sterol selected from the group consisting of cholesterol, cholesterol derivatives, hydrocortisone, phytosterol, and mixtures thereof, and oil. The term "cholesterol derivatives," as used herein, includes but is not limited to sulfate and phosphate derivatives of cholesterol. Preferred sterols include phytosterols, such as soya sterol.

Glycerol esters for use in the invention include, but are not limited to, glycerol monooleate (GMO), glycerol monostearate (GMS), glycerol trioleate (GTO), glycerol monolaurate (GML), and glycerol dilaurate (GDL). Preferred glycerol esters of the invention are GMO and GMS.

Oils useful in forming antibacterial oil-in-water emulsions of the present invention include a broad spectrum of water-immiscible materials, such as soybean oil, avocado oil, squalene oil, sesame oil, olive oil, canola oil, corn oil, rapeseed oil, safflower oil, sunflower oil, fish oils, flavored oils, water insoluble vitamins, and mixtures thereof. In one preferred embodiment of the invention, the oil is a scented or flavored oil, such as peppermint oil.

In preferred embodiments, the emulsion further comprises a positive or negative charge producing agent. Positive charge producing agents for use in the invention preferably include cationic halogen-containing compounds having a $C_{12}$–$C_{16}$ chain. In one preferred embodiment, the cationic halogen-containing compound having a $C_{12}$–$C_{16}$ chain is selected from the group consisting of cetylpyridinium chloride (CPC), cetylpyridinium bromide (CPB), and cetyltrimethylammonium bromide (CTAB). Other cationic halogen-containing compounds which can be used include, for example, cetyldimethyethylammonium bromide, cetyltrimethylammonium chloride, cetylbenzyldimethylammonium chloride, cetyltributylphosphonium bromide, dodecyltrimethylammonium bromide, and tetradecyltrimethylammonium bromide.

Alternatively, the emulsion may contain a negative charge producing agent. Negative charge producing agents which can be used are anionic compounds having a $C_{12}$–$C_{22}$ chain, preferably organic acids. In a preferred embodiment of the invention, the negative charge producing agent is oleic acid.

Antibacterial oil-in-water emulsions of the present invention can be formed using classic emulsion forming techniques which are well known in the art. In brief, the lipid-oil phase is mixed with the aqueous phase under relatively high shear forces to obtain an oil-in-water emulsion containing oil droplets which are approximately one micron in diameter. More particularly, a lipid-containing oily discontinuous phase is formed by blending (a) an oil carrier; (b) a primary emulsifier, preferably a glycerol ester selected from the group consisting of GMO or GMS; and, optionally, (c) a positive or negative charge producing agent as described above, along with any other compatible amphiphiles or emulsifiers, such as Polysorbate 60, and any sterols or other lipophilic materials to be incorporated into the lipid-oil phase.

Once the lipid-oil phase is formed, it is heated as necessary for flowability and blended with an aqueous phase (e.g., water, saline, or any other aqueous solution which can hydrate the lipids) on a volume to volume basis ranging from about 1:4 to 1:2, preferably about 1:3 lipid-oil phase to aqueous phase. The lipid-oil and aqueous phases can be blended using any apparatus capable of producing the high shear mixing forces, including, for example, a French press, a Novamix™ lipid vesicle maker (IGI Inc., Buena N.J.), a syringe mixer, or, alternatively by hand using two syringes as described in U.S. Pat. Nos. 4,895,452 and 4,911,928, the teachings of which are incorporated by reference herein.

Antibacterial oil-in-water emulsions of the present invention provide the advantage of being stable in the presence of heat, acid, or base. For example, as shown below in Example 4, emulsions of the invention are not significantly altered or broken down when boiled or exposed to 1N Nitric acid or 1N sodium hydroxide. This stability makes the emulsions suitable for pharmaceutical administration, even internal administration.

Antibacterial oil-in-water emulsions of the present invention can be used to inactivate bacteria, particularly gram negative bacteria such as *Helicobacter pylori*, upon contact. For example, the presently disclosed emulsions can be used for oropharyngeal application, as a spray or mouthwash, to inactivate or prevent infection secondary to *Streptococcus pneumoniae*, Group A beta-hemolytic Streptococcus, *Haemophilus influenzae*, and *Neisseria meningitidis*. The presently disclosed emulsions can also be administered orally to inactivate or prevent gastrointestinal infections (e.g., gastritis or peptic ulcer disease) secondary to *Helicobacter pylori*. These emulsions can also be used for venereal application, as a cream, gel, or suppository to inactivate or prevent infection secondary to *Neisseria gonorrhoeae, Gardnerella*

*vaginalis*, and Group B Streptococcus. The presently disclosed emulsions can also be used for dermatological application as a cream or gel to inactivate or prevent infection secondary to *Propionibacterium acnes, Staphylococcus aureus, Staphylococcus epidermidis,* and Group B Streptococcus. In a preferred embodiment of the invention, antibacterial emulsions of the present invention are used to prevent infection by gram negative bacteria, such as *Helicobacter pylori*, with relatively rough LPS types as compared to other gram negative bacteria. In a particularly preferred embodiment of the invention, the emulsions are administered orally to inactivate or prevent gastrointestinal infections (e.g., gastritis or peptic ulcer disease) secondary to *Helicobacter pylori*.

The present invention also provides an antibacterial preparation suitable for pharmaceutical administration consisting of the antibacterial emulsion and a pharmaceutically acceptable carrier. The term "pharmaceutically acceptable carrier," as used herein, refers to any physiologically compatible carrier which is suitable for pharmaceutical administration. Use of such media and agents for pharmaceutically active substances is well known in the art. Except insofar as any conventional media or agent is incompatible with the emulsions of the present invention, use thereof in a pharmaceutical preparation is contemplated.

The present invention further provides methods for inhibiting the growth of a bacterium, particularly *Helicobacter pylori*, either in vivo or in vitro, by topical or systemic administration of the antibacterial emulsion of the present invention. Accordingly, another aspect of the invention provides a method for preventing or treating infection by a bacterium, preferably *Helicobacter pylori*. The term "topical," as used herein, includes application to mucous membranes, oral surfaces, skin, inner ear surfaces, or the surfaces of any bodily orifice, such as the vagina or rectum. The term "systemic", as used herein, includes any form of internal administration, including but not limited to, oral and intravenous administration.

The following examples will illustrate the efficacy of the invention.

EXAMPLE 1

Preparation of GMO and GMS Oil-in-Water Emulsions

In this Example, a series of positively charged, negatively charged, and chargeless oil-in-water emulsions having either GMO or GMS as the primary emulsifier were formed. Selected emulsions were also characterized with regard to purity, pH and size of oil droplets.

Table 1 shows the amount of each chemical component used to form the lipid-oil phase of several positively charged GMO and GMS oil-in-water emulsions having glycerol monooleate (GMO) or glycerol monostearate (GMS) as the primary emulsifiers and cetylpyridinium chloride (CPC), cetylpyridinium bromide (CPB), cetyltrimethylammonium bromide (CTAB), or dimethyldioctadecylammonium bromide (DDDAB) as positive charge producing agents.

TABLE 1

|  | GMO/CPC | GMO/CPB | GMO/CTAB | GMS/CPC | GMS/DDDAB |
|---|---|---|---|---|---|
| GMO | 3.43 g | 3.43 g | 3.43 g | — | — |
| GMS | — | — | — | 3.43 g | 3.43 g |

TABLE 1-continued

|  | GMO/CPC | GMO/CPB | GMO/CTAB | GMS/CPC | GMS/DDDAB |
|---|---|---|---|---|---|
| Soya Sterol or cholesterol | 0.96 g | 0.96 g | 0.96 g | 0.96 g | 0.96 g |
| Tween 60 | 0.84 g | 0.84 g | 0.84 g | 0.84 g | 0.84 g |
| Soybean Oil | 11 g | 11 g | 11 g | 11 g | 11 g |
| CPC | 130 mg | — | — | 130 mg | — |
| CPB | — | 150 mg | — | — | — |
| CTAB | — | — | 140 mg | — | — |
| DDDAB | — | — | — | — | 240 mg |

To prepare the positively charged emulsions shown above in Table 1, a lipid-oil phase containing approximately 12 to 21% by weight GMO or GMS, 0.8 to 0.9% by weight cationic halogen-containing compound, 67 to 80% by weight carrier oil such as soybean oil, 3 to 5% by weight Tween 60 (Polyoxyethylene 20 sorbitan monostearate), and 3 to 6% by weight soya sterol was heated for approximately one hour at 86° C. The lipid-oil phase was then blended with an aqueous phase containing water at 65° C. using a 5 ml syringe machine as described in U.S. Pat. No. 4,895,452 on a volume to volume basis of 13 parts lipid-oil to 37 parts water.

Table 2 shows the amount of each chemical component used to form the lipid-oil phase of negatively charged GMO and GMS oil-in-water emulsions having glycerol monooleate (GMO) or glycerol monostearate (GMS) as the primary lipids and oleic acid as a negative charge producing agent.

TABLE 2

|  | GMO | GMO | GMS |
|---|---|---|---|
| GMO | 3.43 g | 3.43 g | — |
| GMS | — | — | 6.86 g |
| Soya Sterol or cholesterol | 0.96 g | 0.96 g | 1.92 g |
| Tween 60 | 0.84 g | 0.84 g | 2.82 g |
| Soybean Oil | 22 g | 11 g | 24.1 g |
| Oleic Acid | 108 mg | 108 mg | 216 mg |

To prepare the negatively charged emulsions shown above in Table 2, a lipid-oil phase containing approximately 12 to 21% by weight GMO or GMS, 67 to 80% by weight carrier oil such as soybean oil, 5 to 8% by weight Tween 60 (Polyoxyethylene 20 sorbitan monostearate), 5 to 6% by weight soya sterol, and 0.4 to 0.7% oleic acid was heated for approximately one hour at 86° C. The lipid-oil phase was then blended with an aqueous phase containing water at 65° C. using a 5 ml syringe machine as described in U.S. Pat. No. 4,895,452 on a volume to volume basis of 13 parts lipid-oil to 37 parts water.

Table 3 shows the amount of each chemical component used to form the lipid-oil phase of GMO and GMS oil-in-water emulsions having no charge.

TABLE 3

|  | GMO | GMS |
|---|---|---|
| GMO | 3.43 g | — |
| GMS | — | 3.43 g |
| Soya Sterol or cholesterol | 0.96 g | 1.92 g |
| Tween 60 | 0.84 g | 0.84 g |
| Soybean Oil | 22 g | 22 g |

To prepare the chargeless emulsions shown above in Table 3, a lipid-oil phase containing approximately 12 to 13% by weight GMO or GMS, 78 to 80% by weight carrier oil such as soybean oil, 3% by weight Tween 60 (Polyoxyethylene 20 sorbitan monostearate), and 3 to 7% by weight soya sterol was heated for approximately one hour at 86° C. The lipid-oil phase was then blended with an aqueous phase containing water at 65° C. using a 5 ml syringe machine as described in U.S. Pat. No. 4,895,452 on a volume to volume basis of 13 parts lipid-oil to 37 parts water.

Table 4 shows the pH of selected positively and negatively charged emulsions from Tables 1 and 2. Also shown is the size of the lipid-oil droplets of the emulsions measured on a Coulter LS 130 laser sizing instrument equipped with a circulating water bath.

TABLE 4

| Chemical Components of Emulsion | Charge | pH | Mean Coulter Size in Microns | Mean Coulter Range in Microns |
|---|---|---|---|---|
| GMO/CPC | Positive | 3.72 | 1.049 | 0.720–1.401 |
| GMO/CPB | Positive | 4.31 | 0.891 | 0.680–1.124 |
| GMO/CTAB | Positive | 4.82 | 1.143 | 0.647–1.358 |
| GMS/DDDAB | Positive | 5.86 | 1.080 | 0.694–1.532 |
| GMO/Oleic acid | Negative | 4.45 | 1.078 | 0.738–1.448 |
| GMS/CPC | Positive | 3.72 | 1.047 | 0.677–1.497 |

EXAMPLE 2

Preparation of 10 N GMO Oil-in-Water Emulsions

In this Example, a series of positively charged oil-in-water emulsions were prepared having GMO as the primary emulsifier and a 10-fold higher percentage (10 N) of cationic halogen-containing compound (cetylpyridinium chloride (CPC), cetylpyridinium bromide (CPB), cetyltrimethylammonium bromide (CTAB), cetyldimethyethylammonium bromide (CDEAB), and benzalkonium chloride (BAC)), as compared with Example 1, as a positive charge producing agent.

Table 5 shows the amount of each chemical component used to form the lipid-oil phase of the positively charged 10 N GMO emulsions.

TABLE 5

| | Positively Charged 10N Emulsions | | | | |
|---|---|---|---|---|---|
| Chemical Components of Emulsion | GMO/ CPC | GMO/ CPB | GMO/ CTAB | GMO/ CDEAB | GMO/ BAC |
| GMO | 3.43 g | 3.43 g | 3.43 g | 3.43 g | 3.43 g |
| Soya Sterol or cholesterol | 0.96 g | 0.96 g | 0.96 g | 0.96 g | 0.96 g |
| Tween 60 | 0.84 g | 0.84 g | 0.84 g | 0.84 g | 0.84 g |
| Soybean Oil | 11 g | 11 g | 11 g | 11 g | 11 g |
| CPC | 1.3 g | — | — | — | — |
| CPB | — | 1.5 g | — | — | — |
| CTAB | — | — | 1.4 g | — | — |
| CDEAB | — | — | — | 1.3 g | — |
| BAC | — | — | — | — | 1.3 g |

To prepare the 10 N emulsions shown above in Table 3, a lipid-oil phase containing approximately 19% by weight GMO, 62% by weight carrier oil such as soybean oil, 4.7% by weight Tween 60 (Polyoxyethylene 20 sorbitan monostearate), 5.4% by weight soya sterol, and 7.4 to 8.4% by weight cationic detergent was heated for approximately one hour at 86° C. The lipid-oil phase was then blended with an aqueous phase containing water at 65° C. using a 5 ml syringe machine (as described in U.S. Pat. No. 4,895,452) on a volume to volume basis of 13 parts lipid-oil to 37 parts water.

EXAMPLE 3

Microbicidal Activity Against Helicobacter Pylori

In this Example, selected positively charged, negatively charged, and chargeless GMO and GMS emulsions from Tables 1–3 and 5 were tested for antibacterial activity against five different *Helicobacter pylori* isolates from the American Type Culture Collection. The microbicidal assay used was as follows:

Lyophilized *Helicobacter pylori* isolates were obtained from the American Type Culture Collection (ATCC). To the lyophilized culture, 0.5 ml of Schaedler's Broth was added and the entire contents of the vial inoculated to a 5% Sheep blood agar plate (TSA 11). Cultures were then incubated in an anaerobic jar with Campy GasPAK at 37° C. for 72 hours. Colonies from 72 hour TSA 11 plates were then inoculated into Schaedler's broth until an 0.5 McFarland Standard was achieved.

A 1 ml aliquot of the bacterial culture was then mixed with 1 ml of oil-in-water emulsion for 10 minutes. Quantitative cultures were then performed in duplicate on each mixture, and a quantitative culture was performed on the original broth culture. Plates containing bacteria were incubated at 37° C. for 72 hours in an anaerobic jar with Campy GasPaks and then counted. The percentage of bacteria killed were determined by the following equation and the results are shown in Table 6:

$$\% \text{ Kill} = \frac{(A - B)}{A} \times 100$$

A=The total number of bacteria inoculated

B=The number counted after mixing with an emulsion or liposomes

TABLE 6

| Helicobacter Isolate/ Incubation time | GMO/ CPC % kill | GMO/ OA % kill | GMO % kill | GMS/ CPC % kill | GMS/OA % kill | GMS % kill |
|---|---|---|---|---|---|---|
| *Helicobacter pylori* ATCC 43579/10 minutes | 100% | 100% | 100% | 100% | 100% | 99.42 |
| *Helicobacter pylori* ATCC 43579/30 minutes | 100% | 100% | 100% | 100% | 100% | 99.42 |
| *Helicobacter pylori* ATCC 43526/10 minutes | 100% | 100% | 100% | 100% | 100% | 50% |
| *Helicobacter pylori* ATCC 43526/30 minutes | 100% | 100% | 100% | 100% | 100% | 100% |
| *Helicobacter pylori* ATCC 49503/10 minutes | 100% | 100% | 100% | 100% | 100% | 65% |
| *Helicobacter pylori* ATCC 49503/30 minutes | 100% | 100% | 100% | 100% | 100% | 100% |
| *Helicobacter pylori* ATCC 43629/10 minutes | 100% | 100% | 100% | 88.93% | 2.12% | 34.04% |
| *Helicobacter pylori* ATCC 43629/30 minutes | 100% | 100% | 100% | 97.87% | 0% | 51.06% |
| *Heliobacter pylori* ATCC 43504/10 minutes | 100% | 100% | 100% | 93.30% | 93.33% | 87.30% |
| *Helicobacter pylori* ATCC 43504/30 minutes | 100% | 100% | 100% | 100% | 100% | 100% |

Table 6 shows that three of the emulsions (GMO/CPC, GMO/OA, and GMO) totally inactivated all five *Helicobacter pylori* isolates after a 10 minute exposure. These three emulsions each had a different charge (i.e., positive charge (cetylpyridinium chloride), negative charge (oleic acid), and no charge (only GMO)). The other emulsions tested and shown in Table 6 also had significant activity against the various isolates.

Table 7 lists the percentages of *Helicobacter pylori* (ATCC No. 43579) killed after a 10 minute incubation of $5 \times 10^6$ CFU/ml (Trial #1) or $2 \times 10^6$ CFU/ml (Trial #2) bacteria with the 10 N GMO/CPC emulsion from Table 5. The 10 N GMO/CPC emulsion was tested in undiluted form and in several dilutions, as indicated in Table 7.

TABLE 7

| Bacterium | Dilution | Trial #1 | Trial #2 |
|---|---|---|---|
| *Helicobacter pylori* 43579 10 minute incubation | Undiluted | 100.00% | 100.00% |
| | 1:10 | 100.00% | 100.00% |
| | 1:20 | 100.00% | 100.00% |
| | 1:40 | 99.00% | 99.00% |
| | 1:80 | 99.20% | 99.00% |

Table 7 shows that at 10 minutes there is 99 to 100% inactivation of Helicobacter pylori tested with the 10 N GMO/CPC emulsion. Table 7 also shows that the 10 N GMO/CPC emulsion retains 100% of its efficacy when diluted up to 1:20, 99% of its efficacy when diluted up to 1:40, and 99 to 99.2% of its efficacy when diluted up to 1:80.

EXAMPLE 4

Stability of Oil-in-Water Emulsions

In this Example, the GMO/CPC emulsion shown in Table 1 was tested for stability in the presence of heat, acid and base. Table 8 shows the effect of (a) boiling for one hour on breakdown or aggregation of the GMO/CPC emulsion, (b) mixing equal volumes of 1 N nitric acid and GMO/CPC emulsion for two hours on breakdown or aggregation of the GMO/CPC emulsion, and (c) mixing equal volumes of 1 N sodium hydroxide and GMO/CPC emulsion for two hours on breakdown or aggregation of the GMO/CPC emulsion.

TABLE 8

| Chemical Components of Emulsion | Intervention | Mean Coulter Size in Microns | Mean Coulter Range in Microns |
|---|---|---|---|
| GMO/CPC | No boiling | 1.008 | 0.720–1.337 |
| GMO/CPC | Boiling 1 hour | 1.167 | 0.654–1.517 |
| GMO/CPC | No acid treatment | 1.008 | 0.720–1.337 |
| GMO/CPC | 1N $HNO_3$ for 2 hours | 1.062 | 0.675–1.569 |
| GMO/CPC | No base treatment | 1.008 | 0.720–1.337 |
| GMO/CPC | 1N NaOH for 2 hours | 0.804 | 0.658–0.969 |

Table 8 shows that: (a) boiling for 1 hour does not significantly alter the breakdown or size of the GMO/CPC emulsion; (b) 1 N nitric acid exposure for 2 hours does not significantly alter the size or aggregate profile of the GMO/CPC emulsion; and (c) 1 N sodium hydroxide exposure for 2 hours causes a 20% decrease in the mean size of the GMO/CPC emulsion without disrupting the emulsion or causing aggregation.

From the above-described Examples 1–4, it is evident that the positively charged, negatively charged, and chargeless antibacterial oil-in-water emulsions of the present invention have significant microbicidal activity against a variety of *Helicobacter pylori* isolates. Furthermore, the emulsions of the invention are stable in the presence of heat, acid, and base, making them very suitable for pharmaceutical administration, whether topical, oral or systemic.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting the growth of *Helicobacter pylori* in an individual comprising the step of systemically administering to the individual an antibacterial oil-in-water emulsion, said antibacterial emulsion being in the form of droplets of an oily discontinuous phase dispersed in a continuous aqueous phase, the emulsion comprising:

a. an oil; and b. glycerol monooleate.

2. The method of claim 1 wherein the oily discontinuous phase further comprises a cationic halogen-containing compound having a $C_{12}$–$C_{16}$ chain.

3. The method of claim 1 wherein the oily discontinuous phase further comprises an negative charge producing agent having a $C_{12}$–$C_{22}$ chain.

4. The method of claim 1 wherein the oil is selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof.

5. The method of claim 1 wherein the oily discontinuous phase further comprises at least one sterol selected from the group consisting of cholesterol, cholesterol derivatives, hydrocortisone, phytosterol, and mixtures thereof.

6. The method of claim 2 wherein the halogen is selected from the group consisting of chlorine, bromine, and fluorine.

7. The method of claim 6 wherein the cationic halogen-containing compound having a $C_{12}$–$C_{16}$ chain is selected from the group consisting of cetylpyridinium chloride, cetylpyridinium bromide, cetyltrimethylammonium bromide, cetyldimethyethylammonium bromide, cetyltrimethylammonium chloride, cetylbenzyldimethylammonium chloride, cetyltributylphosphonium bromide, dodecyltrimethylammonium bromide, and tetradecyltrimethylammonium bromide.

8. The method of claim 3 wherein the negative charge producing agent is oleic acid.

9. The method of claim 1 wherein the step of systemically administering comprises oral administration.

* * * * *

UNITED STATES PATENT AND TRADEMARK OFFICE
CERTIFICATE OF CORRECTION

PATENT NO. : 5,618,840
DATED : April 8, 1997
INVENTOR(S) : D. Craig Wright, M.D.

It is certified that error appears in the above-indentified patent and that said Letters Patent is hereby corrected as shown below:

At column 3, line 21 delete ".priori" and insert --pylori--.

Signed and Sealed this

Twelfth Day of August, 1997

Attest:

Attesting Officer

BRUCE LEHMAN

Commissioner of Patents and Trademarks